United States Patent
Born

(10) Patent No.: US 9,320,668 B1
(45) Date of Patent: *Apr. 26, 2016

(54) EXTREMITY SURGICAL SUPPORT DEBRIDEMENT PLATFORM

(71) Applicant: Christopher T. Born, Providence, RI (US)

(72) Inventor: Christopher T. Born, Providence, RI (US)

(*) Notice: Subject to any disclaimer, the term of this patent is extended or adjusted under 35 U.S.C. 154(b) by 36 days.

This patent is subject to a terminal disclaimer.

(21) Appl. No.: 13/844,430

(22) Filed: Mar. 15, 2013

Related U.S. Application Data

(63) Continuation-in-part of application No. 12/837,144, filed on Jul. 15, 2010, now Pat. No. 8,434,491.

(60) Provisional application No. 61/225,845, filed on Jul. 15, 2009.

(51) Int. Cl.
    *A61G 13/10* (2006.01)

(52) U.S. Cl.
    CPC .................. *A61G 13/102* (2013.01)

(58) Field of Classification Search
    CPC .............................. A61G 13/102; A61M 1/008
    USPC .............. 128/845, 846, 869, 879, 880; 5/606, 5/646, 647, 900, 928; 604/317, 356, 541; 4/606, 607, 609
    See application file for complete search history.

(56) References Cited

U.S. PATENT DOCUMENTS

| | | | |
|---|---|---|---|
| 561,514 A | 6/1896 | Lichtenstein | |
| 2,609,261 A | 9/1952 | Parker | |
| 2,945,731 A | 7/1960 | Tutrone | |
| 3,328,024 A | 6/1967 | Weil | |
| 4,082,257 A * | 4/1978 | Strickland | 5/647 |
| 4,243,214 A * | 1/1981 | LaRooka | 5/630 |
| 4,602,773 A | 7/1986 | Craven, Jr. | |
| 4,650,171 A | 3/1987 | Howorth | |
| 4,718,653 A * | 1/1988 | Rothman | 5/658 |
| 4,772,002 A | 9/1988 | McConnell et al. | |
| 4,947,418 A | 8/1990 | Barr et al. | |
| 5,114,416 A | 5/1992 | Karwoski et al. | |
| 5,173,346 A | 12/1992 | Middleton | |
| 6,102,073 A * | 8/2000 | Williams | 137/602 |
| 6,490,742 B2 | 12/2002 | Hall et al. | |
| 6,562,013 B1 * | 5/2003 | Marasco, Jr. | 604/290 |
| 6,609,257 B1 | 8/2003 | O'Geary | |
| 6,935,341 B2 * | 8/2005 | Musso et al. | 128/849 |
| 6,938,639 B1 * | 9/2005 | Robinson | 137/312 |
| 7,131,965 B1 * | 11/2006 | Thornbury et al. | 604/356 |

(Continued)

FOREIGN PATENT DOCUMENTS

| | | |
|---|---|---|
| CH | 37751 | 9/1906 |
| WO | 03061505 A1 | 7/2003 |

*Primary Examiner* — Nicholas Woodall
*Assistant Examiner* — Raymond E Harris
(74) *Attorney, Agent, or Firm* — Adler Pollock & Sheehan P.C.; Daniel J. Holmander, Esq.; George N. Chaclas, Esq.

(57) ABSTRACT

The present invention provides a surgical support debridement platform for extremities of a human or mammal to assist a physician in treating such extremity. The platform generally includes a body member. The body member includes a bottom end and at least one side wall. The body member defines an interior volume for temporarily containing fluid. In operation, the extremity is positioned upon an upper surface of the platform to facilitate the process of debridement and lavage of extremities.

19 Claims, 18 Drawing Sheets

(56) References Cited

U.S. PATENT DOCUMENTS

| | | |
|---|---|---|
| 7,640,610 B2 | 1/2010 | Mervar |
| 2002/0092563 A1* | 7/2002 | Robinson ................. 137/312 |
| 2002/0151834 A1 | 10/2002 | Utterberg |
| 2006/0286334 A1* | 12/2006 | Harpole ................... 428/43 |
| 2007/0032764 A1 | 2/2007 | Lampropoulos |
| 2008/0306458 A1 | 12/2008 | Chandrasekar et al. |

* cited by examiner

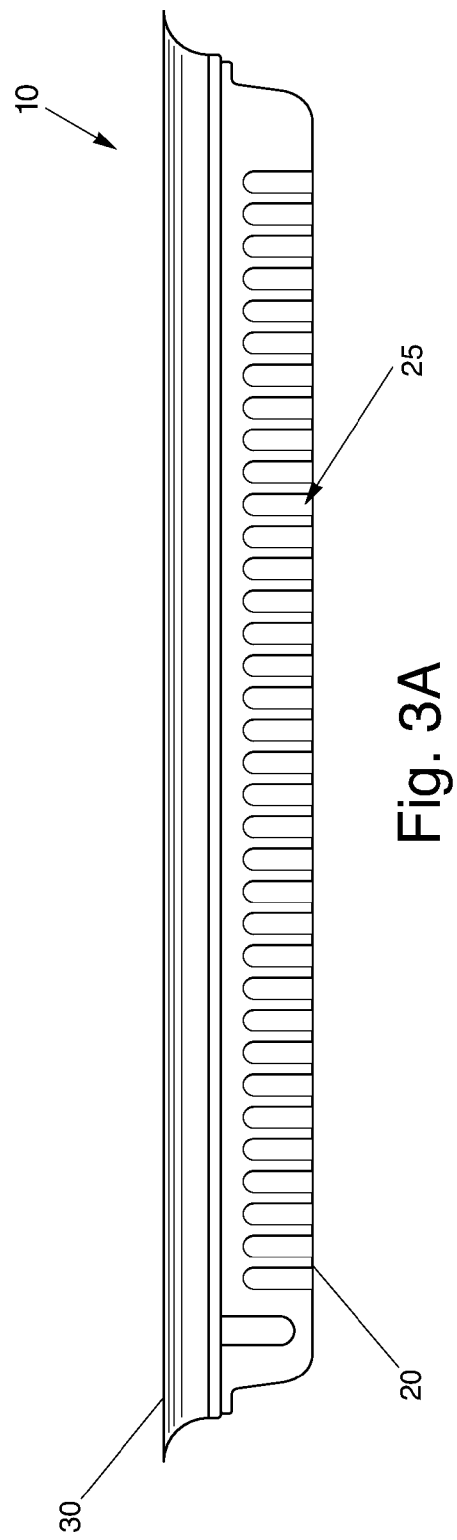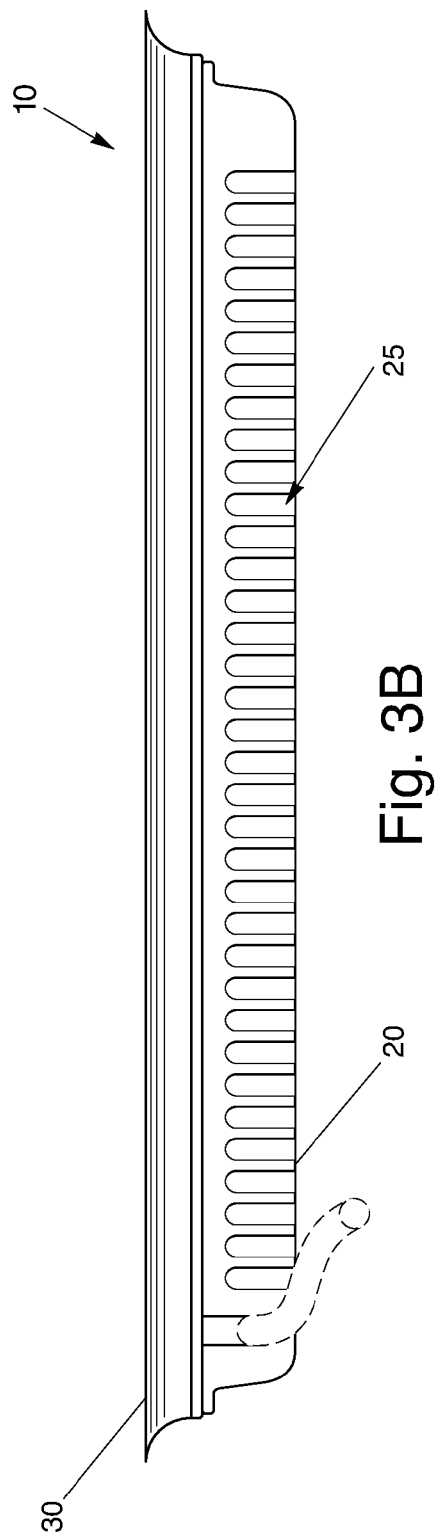

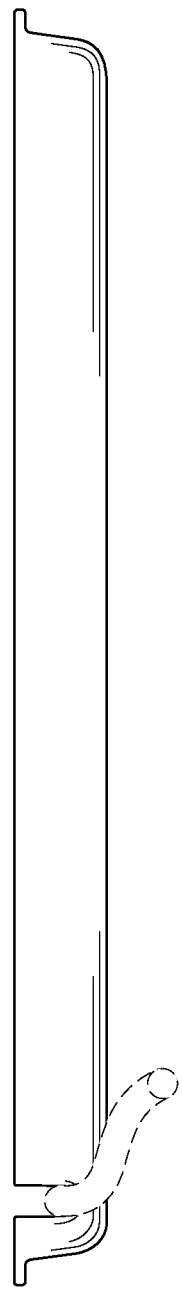
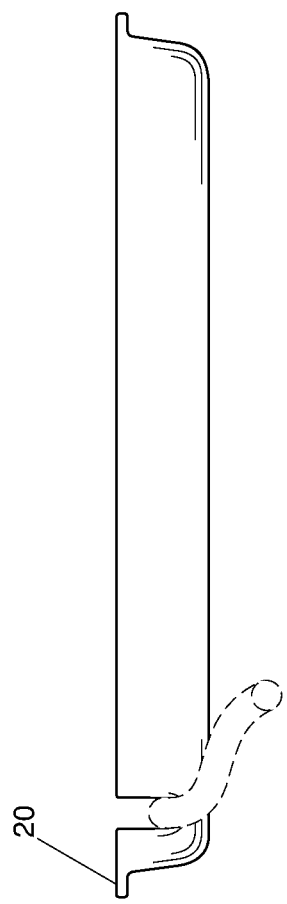
Fig. 5A
Fig. 5B

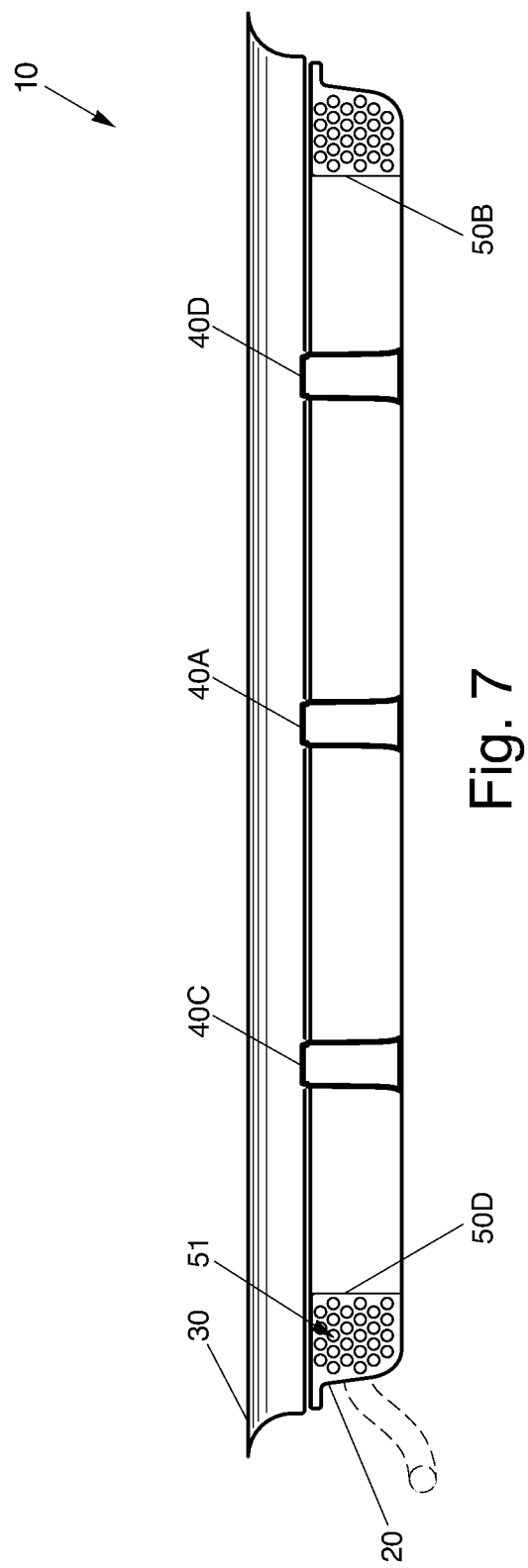

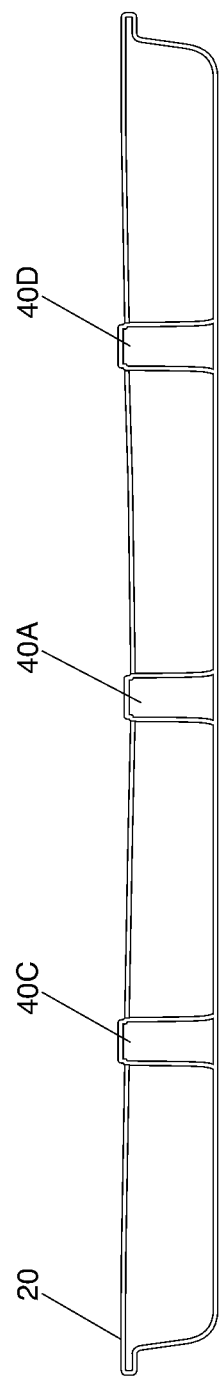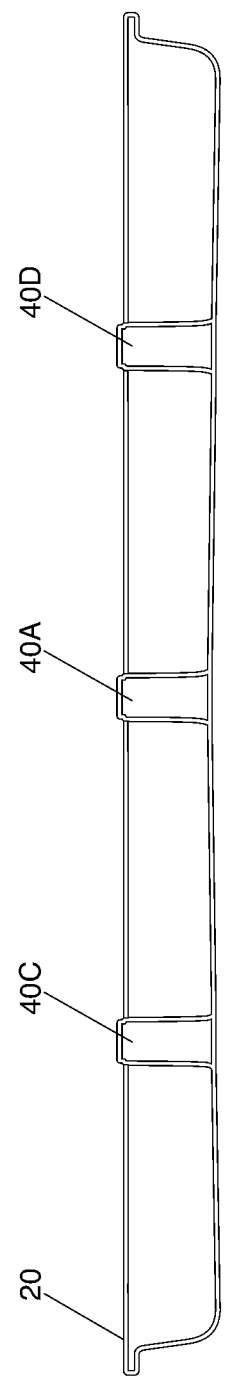

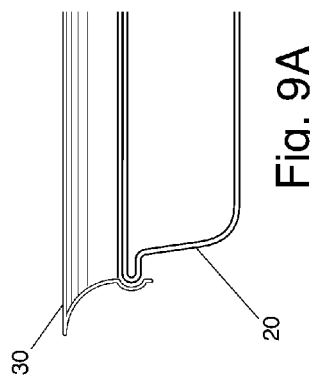
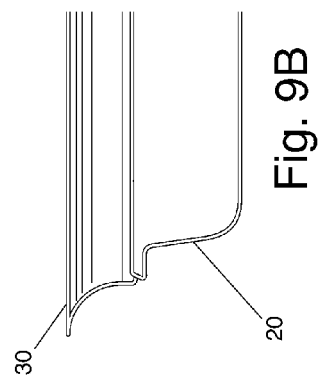
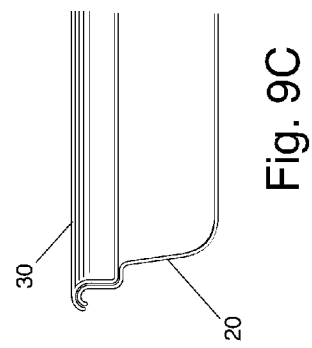

EXTREMITY SURGICAL SUPPORT DEBRIDEMENT PLATFORM

CROSS REFERENCE TO RELATED APPLICATIONS

This continuation-in-part application is related to and claims priority from earlier filed, U.S. Non-Prov. application Ser. No. 12/837,144 filed Jul. 15, 2010, and U.S. Provisional Patent Application No. 61/225,845 filed Jul. 15, 2009, all of which is incorporated herein by reference.

BACKGROUND OF THE INVENTION

The present invention generally relates to surgical accessories and more particularly to a device that would allow support of an extremity during surgical and debridement procedures by medical personnel. More specifically, the present invention relates to an extremity surgical support debridement platform used to facilitate the process of debridement and lavage of injured extremities.

Surgical accessories adopted to allow medical personnel to perform medical treatment on a patient or a portion of a patient while collecting waste fluid or the like generated from such treatment are known. The most common type being a simple basin or towel. Other more complicated and expensive accessories are also known as discussed below.

U.S. Pat. No. 561,514 shows a bandaging table with a single liquid permeable surface containing several cutouts which receive medical instruments or other items required during the bandaging procedure.

U.S. Pat. No. 2,609,261 shows a collapsible limb support which includes a screen surface with access to a drip pan.

U.S. Pat. No. 2,945,731 shows a surgical drainage attachment for use with a standard operating table. This attachment comprises of a basin with a screen on top thereof for support of the hand or foot of a patient.

U.S. Pat. No. 3,328,024 shows a drainage tray more or less permanently attached to a standard operating table having an upper screen surface and a lower drain opening.

U.S. Pat. No. 4,082,257 shows a surgery table for use on a hand and includes a downwardly sloped upper operating surface with multiple drain holes positioned above a drain pan which includes a hose for removal of liquid wastes.

U.S. Pat. No. 4,243,214 shows a high rectangular pan with multiple operating surfaces formed by moveable grids over a drip pan with a padded cutout for the patient's extremity.

It is always recommended to debride and wash out traumatic wounds and infections or to irrigate elective surgical sites of either the upper or lower extremities in either the operating room or the emergency room. This process always includes the use of saline irrigation in amounts that may vary from a few milliliters to several liters. The prior art does not disclosed a dedicated device into which the fluid can drain while the limb is uniformly supported as this debridement and lavage process takes place. The result is that this fluid frequently will pool on the operating room table or floor adding both a contamination risk and a fall hazard to the surgical environment. The alternative technique that is employed is to use receptacles that are not dedicated to this process but which are commonly available in the surgical or emergency room suites. These often include ring or emesis basins and even bed pans. The limbs are not uniformly supported so that fractures and injured soft tissues undergo further trauma. Alternatively, hospitals may customize steel pans by placing a drain at one end or on the bottom and may also create a grid to go over the pan. These devices are often of insufficient length and/or too deep and prove to be cumbersome with the extremity having to be continually moved on and off the grid between the debridement and lavage components, thereby adding trauma to the tissues. The drains get clogged with tissue. These then have to be cleaned out and the suction re-attached all of which add delay to the procedure.

The disadvantages of the prior art are that they are cumbersome in size, not light in weight and not readily portable. They are not easily stackable for storage purposes and could not easily be included in pre-packaged sterile operating room or military-like field packs. Several require attachment to the operating room table or are too high to allow limb placement on the working surface without significant anatomical distortion of the extremity. Vascular and neural elements within the injured extremity can become kinked or torn as a result of these deformities. Several have high-riding side walls that will impede visualization and surgical access to the extremity during a procedure. The use of a fully circular hole or nozzle in the bottom or the sidewall for introduction or attachment of a drain hose in some makes insertion and removal difficult. Nozzles designed for drain hose attachment become easily clogged with tissue because of their narrow bore and frequently need to be cleared. The complicated nature of the prior art also lends to an increased expense for manufacturing.

Therefore, it is desirable for a medical device to facilitate the process of debridement and lavage of injured extremities that is easy to manipulate by a user, lightweight, portable, stackable, detached, durable, permits clear visualization of extremities, disposable and inexpensive to manufacture.

BRIEF SUMMARY OF THE INVENTION

The present invention preserves the advantages of prior art for debridement platforms. In addition, it provides new advantages not found in currently available debridement platforms and overcomes many disadvantages of such currently available debridement platforms.

The present invention is generally directed to a novel and unique extremity surgical support debridement platform. Most importantly, the debridement platform of the present invention enables the process of debridement and lavage of injured extremities that is easy to manipulate by a user, lightweight, portable, stackable, detached, durable, permits clear visualization of extremities, disposable and inexpensive to manufacture.

The debridement platform is dedicated to the process of debridement and lavage of injured extremities. The key features are that it is low profile, yet long and wide enough to uniformly support the entire limb for the entire debridement and lavage process. There are impediments to visualization or surgical access. Plastic suction tubing commonly used in hospitals is easily removed should it become clogged with tissue, but most of the debrided tissue, in this invention, would be captured by the overlying grid or cover member.

The platform generally includes a body member and a cover member. The invention consists of two pieces that include a shallow pan or body member of a generally rectangular shape having a liquid impervious body and an overlying removable, perforated horizontal work surface platform lid or cover member that are placed together under an extremity of a medical patient during the treatment of an extremity. The cover member and the body member are configured of flexible materials and relatively thin walls to cushion the extremity for comfort. It should be noted that the platform may have a one-piece configuration which is injection molded or two-piece or more configuration. The body member includes a bottom end and at least one side wall. The body member defines an interior volume for temporarily containing fluid.

At least one drainage aperture is defined within the body member for draining the fluid from the interior of the body member. The at least one drainage aperture generally defines a U shape or similar shape for easy removal of a drainage tube positioned therein. The at least one drainage aperture or side-entry portals are positioned proximal to a corner area of the body member where at least one side wall and bottom wall are joined together. The drainage aperture is positioned in lower portion of the sidewall substantially proximal to the bottom end of the body member. The draining apertures are incompletely circularized cutouts to allow the easy introduction of suction or drain hose for removal of fluid from the interior of the body member.

A cover member includes a top end and at least one side wall. The cover member and the body member are releasably engaged to define an overall low profile for easier deployment under an extremity and visibility of the extremity. The cover member defines at least one cover aperture for facilitating a flow of the fluid into interior of the body member. The cover member is perforated by a series of holes large enough to allow for the free flow of blood and other fluids into the underlying body member, yet small enough to prevent large pieces of tissue and other debris from falling into the body member during the procedure. The at least one cover aperture may have a smaller diameter within an extremity area where an extremity is resting on said cover member and a larger diameter outside said extremity area on said cover member to prevent pooling of fluid about the extremity.

The cover member may be configured and customized to accommodate a wide array of extremities for improved performance. The cover member has a low-profile splash guard positioned along an outer periphery of the cover member to prevent fluid from contacting a patient. The splash guard may be molded into the cover member. The cover member may be predefined with a recessed extremity area for providing further stability to extremity while seating on the cover member. Also, the top end of the cover member may have a slightly concave shape to prevent pooling of fluid about an extremity. Likewise, the body member may have a slightly convex shape to facilitate flow of fluid to the drainage apertures.

It is desirable to releasably engage the cover member and the body member which can be accomplished by a variety of methods. For example, a surface of said at least one side wall of the cover member is engaged to a surface of the at least one side wall of the body member to provide support and stability. The cover member may further include a rolled cover lip member for respectively engaging a rolled body lip member of the body member. The rolled cover lip member may nest within an inner surface of the rolled body lip member. Also, the rolled body lip member may nest within an inner surface of the rolled cover lip member. Alternatively, a lower periphery of the cover member may engage an upper periphery of the body member by a variety of methods, such as a friction fit, while still allowing for releasable engagement of the cover member to the body member.

At least one support member is positioned within interior of said body member. The cover member is supported from below by at least one support member or raised portions of the bottom end of the body member acting as uprights that are high enough to have contact with the cover member's undersurface. The at least one support member engages the body member and the cover member to provide stability and support. The at least one support member depends from bottom end of the body member. Alternatively, the at least one support member is defined within the body member in the shape of a tower. In one embodiment, a top portion of the at least one support member is keyed into the at least one cover aperture to prevent sheering of the cover member from the body member. The top portions of the at least one support member interdigits with corresponding at least one cover apertures in the cover member. The top portion of the at least one support member may include an upper region with a recessed shoulder region on either side of the upper region. The cover member seats down slightly into the body member, suspended around its periphery by at least one or more walls of the body member in addition to being supported from below by the at least one support members from the bottom end of the body member. This arrangement prevents side slippage of the cover member, yet allows for easy removal of the cover member during the procedure if required to clear debris or for insertion, removal or cleaning of the drainage tube.

At least one filtration trap may be positioned proximal to the at least one drainage aperture of said body member. To provide additional stability, the filtration trap has a lower profile than the side wall of the body member to engage a top portion of the filtration trap with the cover member for additional stability. In one embodiment, the filtration trap has a height approximately equal to the recessed shoulder region of the at least one support member. The filtration trap may be permanently or releasably attached to the body member. For example, the filtration trap may be clipped or inserted into a grooved area defined within the base member which can be removed for cleaning when clogged with debris.

Furthermore, an open cell material may be positioned proximal to the at least one cover aperture or the at least one draining aperture in the platform to prevent clogging of a drainage tube positioned within the at least one drainage aperture defined within the body member for draining the fluid from the interior of the body member. For example, the open cell material may be a sponge material or mesh material for absorbing the fluid.

A flexible strap member for securing the extremity to the platform may engage at least one cover aperture. The strap member includes a means for fastening at a proximal and distal ends of the strap member within the at least one cover aperture. The means for fastening at a proximal and distal ends of the straps may include fasteners or other devices known in the art. For example, a hook may be used to secure the proximal or distal end of the strap within the at least one cover aperture.

The cover member is sufficiently pliable for curling a portion of the cover member proximal to the at least one drainage aperture to provide access to the interior of the body member for removing clogging debris from the filtration trap and drainage tube while maintaining the extremity on the cover member. By locating the filtration trap, at least one U-shaped drainage aperture, and drainage tube in corner areas of the platform, a physician can more easily remove tube for cleaning and remove debris from the filtration traps.

The platform is made of material selected from a variety of materials including polycarbonate, HDPE (high density polyethylene), low density polyethylene, plastic materials, biodegradable materials, regrind materials, and recycled plastic materials in combination or alone. Also, the platform is injection molded using plastic materials to accommodate a wide range of extremity sizes and types at a lower cost.

A debridement surgical support kit for extremities of a human or mammal to assist a physician in treating an extremity may include the platform, as described herein, along with a surgery medical pack. The platform including the body member and the cover member. The cover member nested with the body member or the body member nested within the cover member to reduce the height of the platform to a lower profile for more efficient transport. The surgery medical pack including means for debridement and lavage of an extremity of a human known in the art such as surgical tools and other known surgical products for debridement and lavage. The surgery medical pack is positioned within an interior of the nested platform to facilitate transport and reduce overall profile. A box having a low profile may be used for containing the nested platform and surgery medical pack for purposes of transporting and storing said kit until required for surgery in a medical facility or storage area. In addition, one or more platforms may be stackable within one another to further reduce consumption of valuable space within a medical facility, especially a surgical environment.

In operation, the extremity is positioned upon an upper surface of the cover member to facilitate the process of debridement and lavage of extremities. The extremity is seated within the predefined recess area for additional support. The strap members are then secured over the top of the extremity within the at least one cover aperture. During cleaning and debridement, the fluid and travels through the at least one cover aperture for temporary storage within an interior of the body member. Next, the fluid passes through the filtration trap to capture any debris which could potentially clog the drainage tube. The fluid then exits the body member through the drainage tube positioned within the drainage aperture. If the drainage tube becomes clogged, a user curls or slightly opens a corner portion of the cover member to reveal a corner area of the body member where the filtration trap can be cleaned in place or removed for cleaning, the draining aperture can be cleaned, and the drainage tube can be removed. Most importantly, the extremity may continue to be positioned on the cover member, if desired, during the cleaning and unclogging of the drainage tube, filtration trap, and drainage aperture.

A portion of the body member may define perforations or cut-outs to facilitate removal of one or more sectional flap areas of the body member. For example, two opposing portions of the body member may be removed or hinged away to provide a defined path to position an extremity within the body member. The sectional flap areas may be hinged outward to remove the side wall portion of the body member. Alternatively, the sectional flap areas may be removed or turned inward to guide an extremity within an interior of the body member. In another embodiment, the body member may be pre-formed with the side wall portions of the body member removed in advance of use.

It is therefore an object of the present invention to provide a platform that is easy to manipulate by a user and provides stability and support to the extremity.

It is a further object of the embodiment to provide a platform that is stackable and easy to transport.

Another object of the embodiment is to provide a platform that is disposable and inexpensive to manufacture.

Another object of the embodiment is to provide a platform that permits clear visualization of extremities.

Another object of the embodiment is to provide a platform that permits easy removal of the cover member during a surgical procedure to clear debris or for insertion, removal or cleaning of the drainage tube.

Other objects, features and advantages of the invention shall become apparent as the description thereof proceeds when considered in connection with the accompanying illustrative drawings.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

FIG. 3A is an elevated side view of the cover member and body member of the debridement platform as shown in FIG. 1 without a drainage tube;

FIG. 3B is an elevated side view of the cover member and body member of the debridement platform as shown in FIG. 1 with a drainage tube;

FIG. 5A is an elevated side view of the body member of the debridement platform as shown in FIG. 3A;

FIG. 5B is an elevated end view of the body member of the debridement platform as shown in FIG. 3A;

FIG. 7 is an elevated cross-sectional side view of the debridement platform as shown in FIG. 1 taken along line 7-7;

FIG. 8A is an elevated cross-sectional side view of another embodiment of debridement platform as shown in FIG. 6A where the cover member has a slight concave shape;

FIG. 8B is an elevated cross-sectional side view of another embodiment of debridement platform as shown in FIG. 6A where the body member has a slight convex shape;

FIG. 9A is partial cross-sectional view of another embodiment of the debridement platform as shown in FIG. 3A;

FIG. 9B is partial cross-sectional view of another embodiment of the debridement platform as shown in FIG. 3A;

FIG. 9C is partial cross-sectional view of another embodiment of the debridement platform as shown in FIG. 3A;

DETAILED DESCRIPTION OF THE PREFERRED EMBODIMENTS

In accordance with the invention, an extremity surgical support debridement platform 10 is provided. The debridement platform enables the process of debridement and lavage of injured extremities that is easy to manipulate by a user, lightweight, portable, stackable, detached, durable, permits clear visualization of extremities, disposable and inexpensive to manufacture.

As shown generally in FIGS. 1-13, the debridement platform 10 is dedicated to the process of debridement and lavage of injured extremities. The key features are that it is low profile, yet long and wide enough to uniformly support the entire limb for the entire debridement and lavage process. There are impediments to visualization or surgical access. Plastic suction tubing commonly used in hospitals is easily removed should it become clogged with tissue, but most of the debrided tissue, in this invention, would be captured by the overlying grid or cover member 30.

The platform 10 generally includes a body member 20 and a cover member 30. The platform 10 consists of two pieces that include a shallow pan or body member 20 of a generally rectangular shape having a liquid impervious body and an overlying removable, perforated horizontal work surface platform lid or cover member 30 that are placed together under an extremity of a medical patient during the treatment of an extremity. The depth of the body member 20 is shallow enough to allow for easy placement under an injured limb without causing undue deformity or pressure but the cover member 30 is of appropriate surface dimensions to provide support. The cover member 30 and the body member 20 are configured of flexible materials and relatively thin walls to cushion the extremity for comfort. It should be noted that the platform 10 may have a one-piece configuration which is injection molded or two-piece or more configuration.

Figure 2:
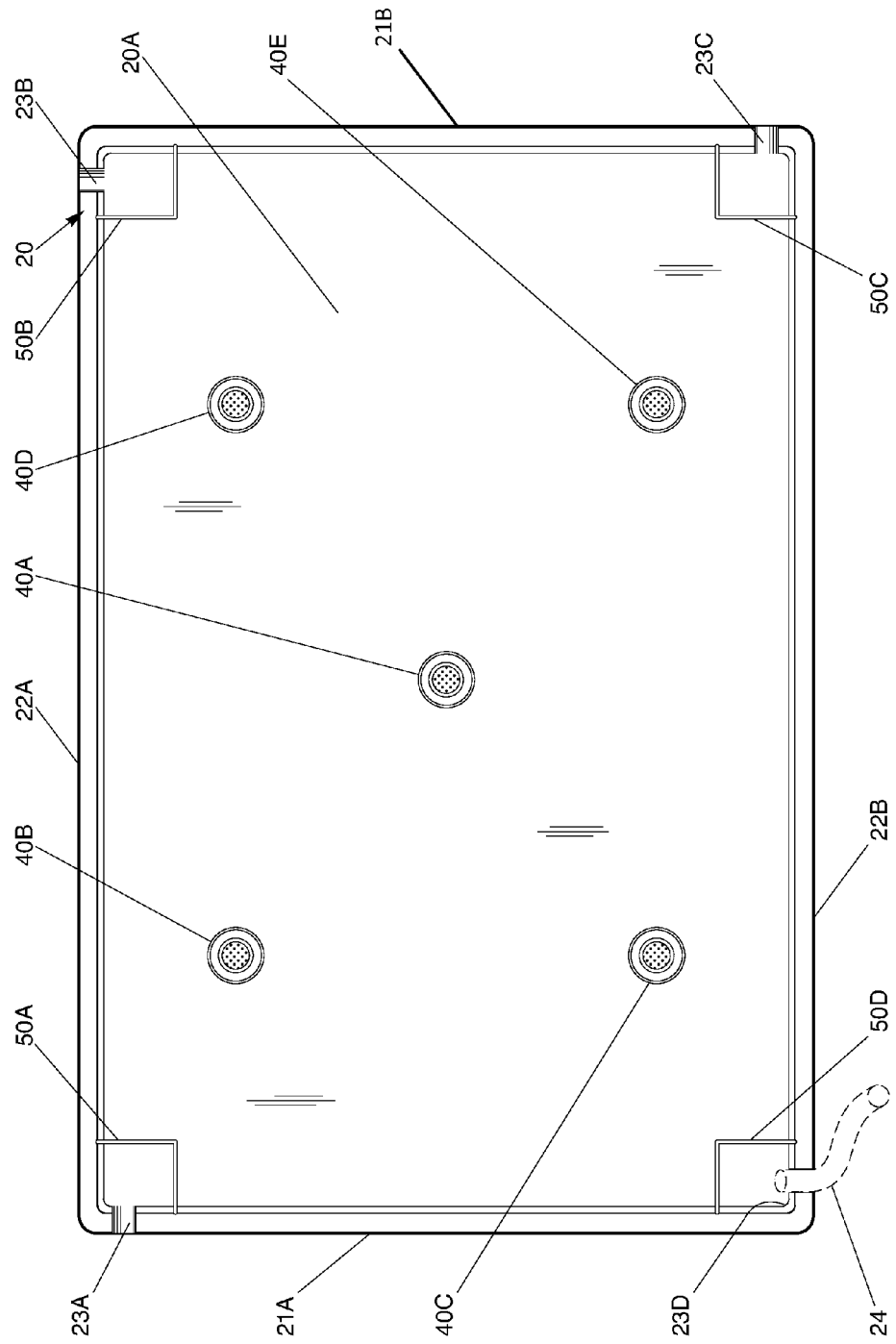
FIG. 2 is a top view of the body member of the debridement platform as shown in FIG. 1.
Figure 4A:
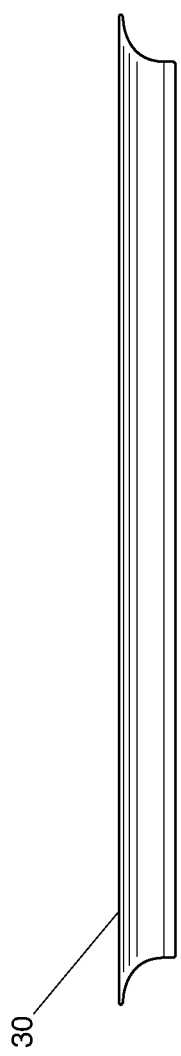
FIG. 4A is an elevated side view of the cover member of the debridement platform as shown in FIG. 1 with a splash guard.
Figure 4B:
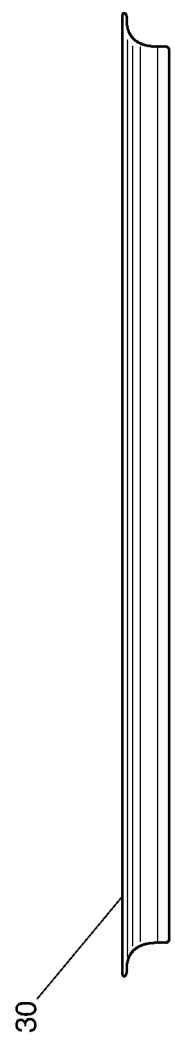
FIG. 4B is an elevated side view of the cover member of the debridement platform without a splash guard having a lower profile than FIG. 4A.

Referring to FIG. 2, the body member 20 includes a bottom end 20A and at least one side wall (21A, 21B, 22A, 22B). The body member 20 defines an interior volume for temporarily containing fluid excess from a surgical procedure or cleaning. In a preferred embodiment, the body member 20 includes a bottom end 20A and four side walls (21A, 21B, 22A, 22B). An outer surface of the four side walls (21A, 21B, 22A, 22B). may include a defined non-slip surface area 25 for better gripping by a user.

Still Referring to FIG. 2, at least one drainage aperture (23A, 23B, 23C, 23D) is defined within the body member 20 for placing a drainage tube 24 for draining the fluid from the interior of the body member 20. The at least one drainage aperture (23A, 23B, 23C, 23D) generally defines a U shape or similar shape for easy removal of the drainage tube 24 positioned therein. The U-shaped cutouts or drainage apertures (23A, 23B, 23C, 23D) at one end of the body member 20 are placed to allow a hose or drainage tube 24 to be passed into the bottom end 20A of the body member 20 to allow for fluid to be drained from the interior of the body member 20. This configuration means that the drainage tube 24 is merely laid into the "U" and does not have to be drawn through a hole or coupled to a nozzle. Of course, if desired, the drainage tube 24 may be connected coupled to a nozzle or drawn through a hole.

The at least one drainage aperture (23A, 23B, 23C, 23D) or side-entry portals are positioned proximal to a corner area of the body member 20 where at least one side wall (21A, 21B, 22A, 22B) and bottom end 20A are joined together. The drainage aperture (23A, 23B, 23C, 23D) is positioned in lower portion of the sidewall (21A, 21B, 22A, 22B) substantially proximal to the bottom end 20A of the body member 20. The draining apertures (23A, 23B, 23C, 23D) are incompletely circularized cutouts to allow the easy introduction of suction or drainage tube 24 for removal of fluid from the interior of the body member 20.

Figure 1:
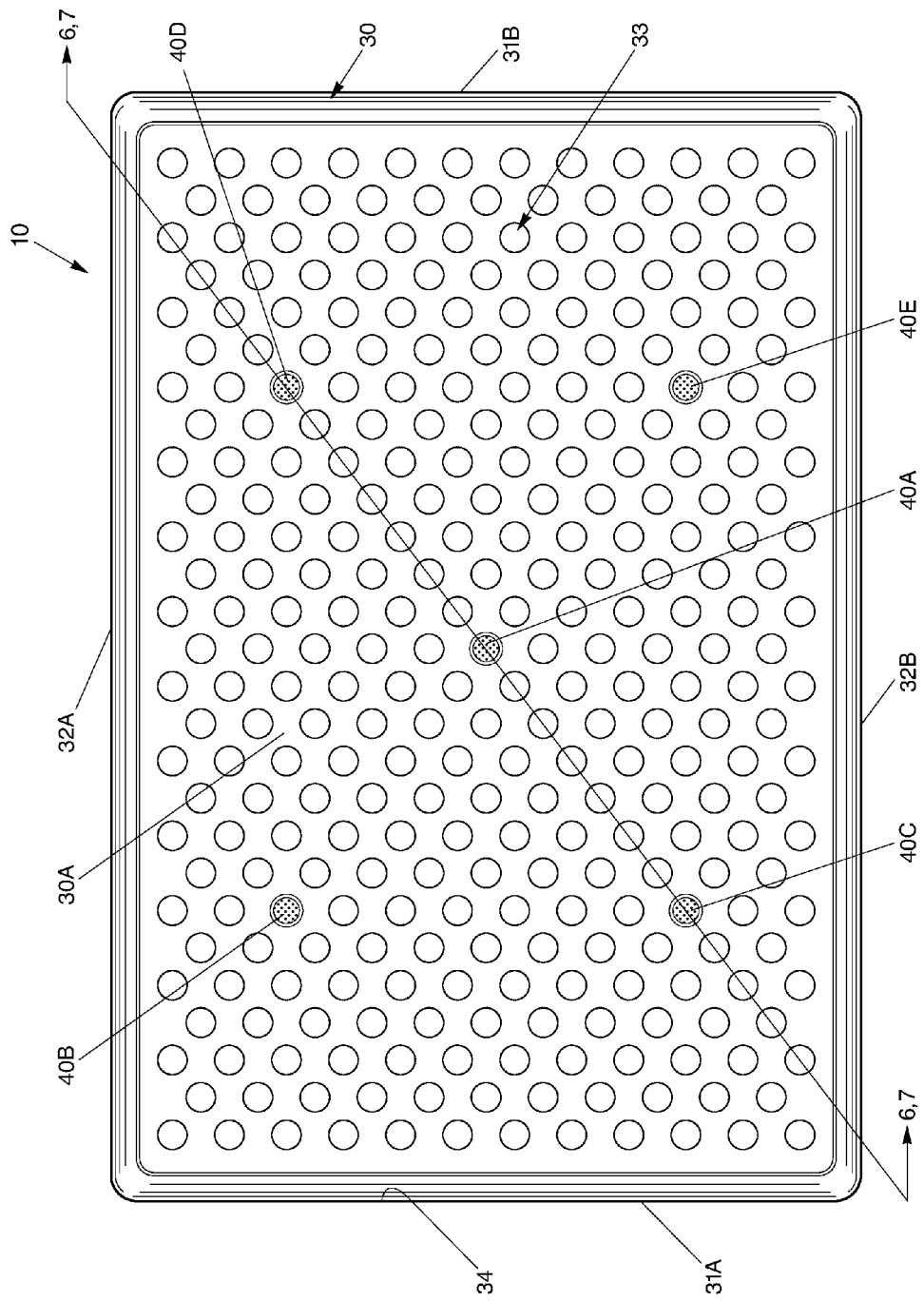
FIG. 1 is top view of the cover member of the described extremity surgical support debridement platform of the present invention.

Referring to FIG. 1, a cover member 30 includes a top end 30A and at least one side wall (31A, 31B, 32A, 32B). In a preferred embodiment, the cover member 30 includes the top end 30A and four side walls (31A, 31B, 32A, 32B). The cover member 30 and the body member 20 are releasably engaged to define an overall low profile for easier deployment under an extremity and visibility of the extremity. In general, the cover member 30 is not typically permanently fixed to the underlying body member 20 and is designed for its easy removal, however, a single piece platform 10 may be used where the cover member 30 is permanently attached to the underlying body member 20. The cover member 30 is rectangular and approximately the same length and width as the body member 20.

The cover member 30 defines at least one cover aperture 33 for facilitating a flow of the fluid into an interior of the body member 20. The cover member 30 is perforated by a series of multiple cover apertures 33 large enough to allow for the free flow of blood, a brisk volume of irrigation fluid, and other fluids into the underlying body member 20, yet small enough to prevent large pieces of tissue and other debris from falling into the body member 20 during the procedure which may block or clog the drainage tube. The at least one cover aperture 33 may have a smaller diameter within a predefined recessed extremity area 35 where an extremity is resting on the cover member 30 and a larger diameter outside the extremity area on the cover member 30 to prevent pooling of fluid about the extremity. Also, the at least one cover aperture 33 may be chamfered to facilitate flow of fluid through the at least one cover aperture 33.

The cover member 30 may be configured and customized to accommodate a wide array of extremities for improved performance. The cover member 30 has a low-profile splash guard 34 positioned along an outer periphery of the cover member 30 to prevent fluid from contacting a patient. The cover member 30 may be predefined with a recessed extremity area 35 (FIG. 10) for providing further stability to extremity while seating on the cover member 30. Referring to FIG. 8A, the top end of the cover member 30 may have a slightly concave shape to prevent pooling of fluid about an extremity. Referring to FIG. 8B, the body member 20 may have a slightly convex shape to facilitate flow of fluid to the drainage apertures. The cover member 30 may also have molded-in channels (not shown) on a top surface of the cover member 30 to lead fluid to at least one cover aperture 33.

It is desirable to releasably engage the cover member 30 and the body member 20 which can be accomplished by a variety of methods. For example, a surface of the at least one side wall of the cover member 30 is engaged to a surface of the at least one side wall of the body member 20 to provide support and stability. A bottom edge of the cover member 30 may further include a rolled cover lip member for respectively engaging a top edge of the body member 20 having a rolled body lip member. Also, the rolled lip cover member 30 may be used for gripping by a user to facilitate handling of the debridement platform.

The edge of the body member 20 has a rolled lip member the undersurface of which matches the top surface of the edge of the underlying body member 20 to allow for nesting of the edge of the cover member 30 onto the edge of the body member 20. The top edge of the body member 20 is designed to have a rolled lip to accommodate the corresponding undersurface lip of an overlying cover member 30. The rolled cover lip member may nest within an inner surface of the rolled body lip member. Also, the rolled body lip member may nest within an inner surface of the rolled cover lip member. Alternatively, a lower periphery of the cover member 30 may engage an upper periphery of the body member 20 by a variety of methods, such as a friction fit, while still allowing for releasable engagement of the cover member 30 to the body member 20. FIGS. 9A-9C illustrates various configurations for attaching the body member 20 and cover member 30 together. In an alternative embodiment of the invention, the edge of the body member 20 and the edge of the cover member 30 are configured to allow them to snap together.

Figure 6A:
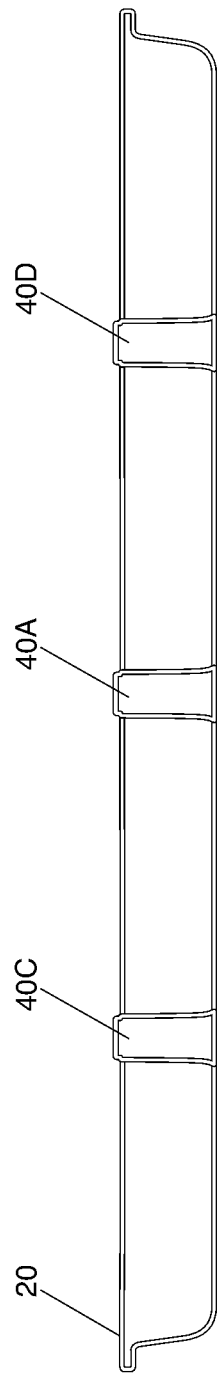
FIG. 6A is an elevated cross-sectional side view of the debridement platform as shown in FIG. 1 taken along line 6-6.
Figure 6B:
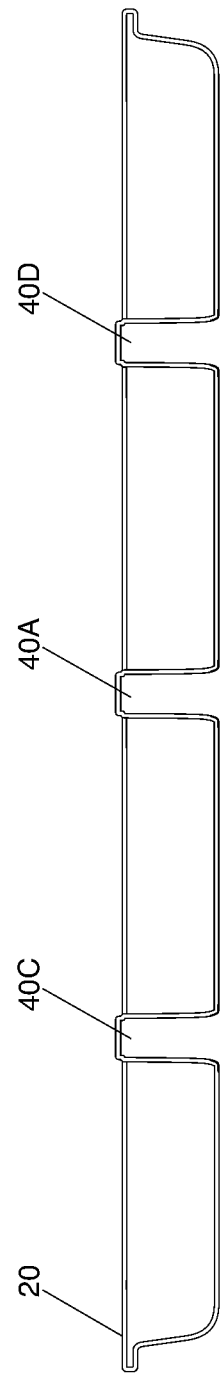
FIG. 6B is an elevated cross-sectional side view of another embodiment of the debridement platform as shown in FIG. 1 taken along line 6-6.

Referring to FIG. 6, At least one support member (40A, 40B, 40C, 40D, 40E) is positioned within interior of the body member 20. For example, there are five support members (40A, 40B, 40C, 40D, 40E) arranged in specific configuration as illustrated in FIG. 2. Note, the at least one support member (40A, 40B, 40C, 40D, 40E) positioned in a central portion of the body member 20 may be slightly shorter in height than the other at least one support members (40A, 40B, 40C, 40D, 40E)s to allow for a slight concavity of the cover member 30. The cover member 30 is supported from below by at least one support member (40A, 40B, 40C, 40D, 40E) or raised portions of the bottom end of the body member 20 acting as uprights that are high enough to have contact with the cover member's 30 undersurface. In one embodiment, the at least one support member (40A, 40B, 40C, 40D, 40E) is in the shape of a cylinder but it is contemplated that the at least one support member (40A, 40B, 40C, 40D, 40E) may be other shapes and sizes other than a cylinder. The at least one support member (40A, 40B, 40C, 40D, 40E) engages the body member 20 and the cover member 30 to provide stability and support. The at least one support member (40A, 40B, 40C, 40D, 40E) depends or arises from the bottom end of the body member 20. Alternatively, the at least one support member (40A, 40B, 40C, 40D, 40E) is defined within the body member 20 in the shape of a tower.

Referring to FIG. 7, in one embodiment, a top portion of the at least one support member (40A, 40B, 40C, 40D, 40E) is keyed into the at least one cover aperture 33 to prevent sheering of the cover member 30 from the body member 20. The top portions of the at least one support member (40A, 40B, 40C, 40D, 40E) interdigitates with corresponding at least one cover aperture 33s in the cover member 30. The top portion of the at least one support member (40A, 40B, 40C, 40D, 40E) may include an upper region with a recessed shoulder region on either side of the upper region. The cover member 30 seats down slightly into the body member 20, suspended around its periphery by at least one or more walls of the body member 20 in addition to being supported from below by the at least one support member (40A, 40B, 40C, 40D, 40E)s from the bottom end of the body member 20. This arrangement prevents side slippage of the cover member 30, yet allows for easy removal of the cover member 30 during the procedure if required to clear debris or for insertion, removal or cleaning of the drainage tube.

At least one filtration trap or more (50A, 50B, 50C, 50D) may be positioned proximal to the at least one drainage aperture (23A, 23B, 23C, 23D). of the body member 20. In a preferred embodiment, there are two filtration traps (50A, 50B, 50C, 50D). Of course, it is contemplated that there may be as many filtration traps (50A, 50B, 50C, 50D) as there are drainage apertures (23A, 23B, 23C, 23D). The filtration trap (50A, 50B, 50C, 50D) includes at least one wall surrounding perimeter of the drainage aperture (23A, 23B, 23C, 23D). In a preferred embodiment, the filtration trap (50A, 50B, 50C, 50D) includes two walls joined together at an angle. Of course, other shapes and positions of the filtration traps (50A, 50B, 50C, 50D) may be used in relation to the location of drainage aperture (23A, 23B, 23C, 23D). To provide additional stability, the filtration trap (50A, 50B, 50C, 50D) has a lower profile than the side wall of the body member 20 to engage a top portion of the filtration trap (50A, 50B, 50C, 50D) with the cover member 30 for additional stability. In one embodiment, the filtration trap (50A, 50B, 50C, 50D) has a height approximately equal to the recessed shoulder region of the at least one support member (40A, 40B, 40C, 40D, 40E). The filtration trap (50A, 50B, 50C, 50D) may be permanently or releasably attached to the body member 20. For example, the filtration trap (50A, 50B, 50C, 50D) may be clipped or inserted into a grooved area defined within the bottom end 20A of the base member 20 which can be removed for cleaning when clogged with debris.

Furthermore, an open cell material may be positioned proximal to the at least one cover aperture 33 or the at least one draining aperture in the platform to prevent clogging of the drainage tube 24 positioned within the at least one drainage aperture (23A, 23B, 23C, 23D) defined within the body member 20 for draining the fluid from the interior of the body member 20. For example, the open cell material may be a sponge material or mesh material for absorbing the fluid.

The at least one wall of the filtration trap (50A, 50B, 50C, 50D) defines at least one filtration aperture 51 for facilitating a flow of the fluid into the drainage aperture (23A, 23B, 23C, 23D) and drainage tube 24. The filtration trap (50A, 50B, 50C, 50D) is perforated by a series of multiple filtration apertures 51 large enough to allow for the free flow of blood, a brisk volume of irrigation fluid, and other fluids into the drainage aperture (23A, 23B, 23C, 23D) and drainage tube 24, yet small enough to prevent large pieces of tissue and other debris from falling into the drainage aperture (23A, 23B, 23C, 23D) and drainage tube 24 which may block or clog the drainage tube 24.

Figure 11:
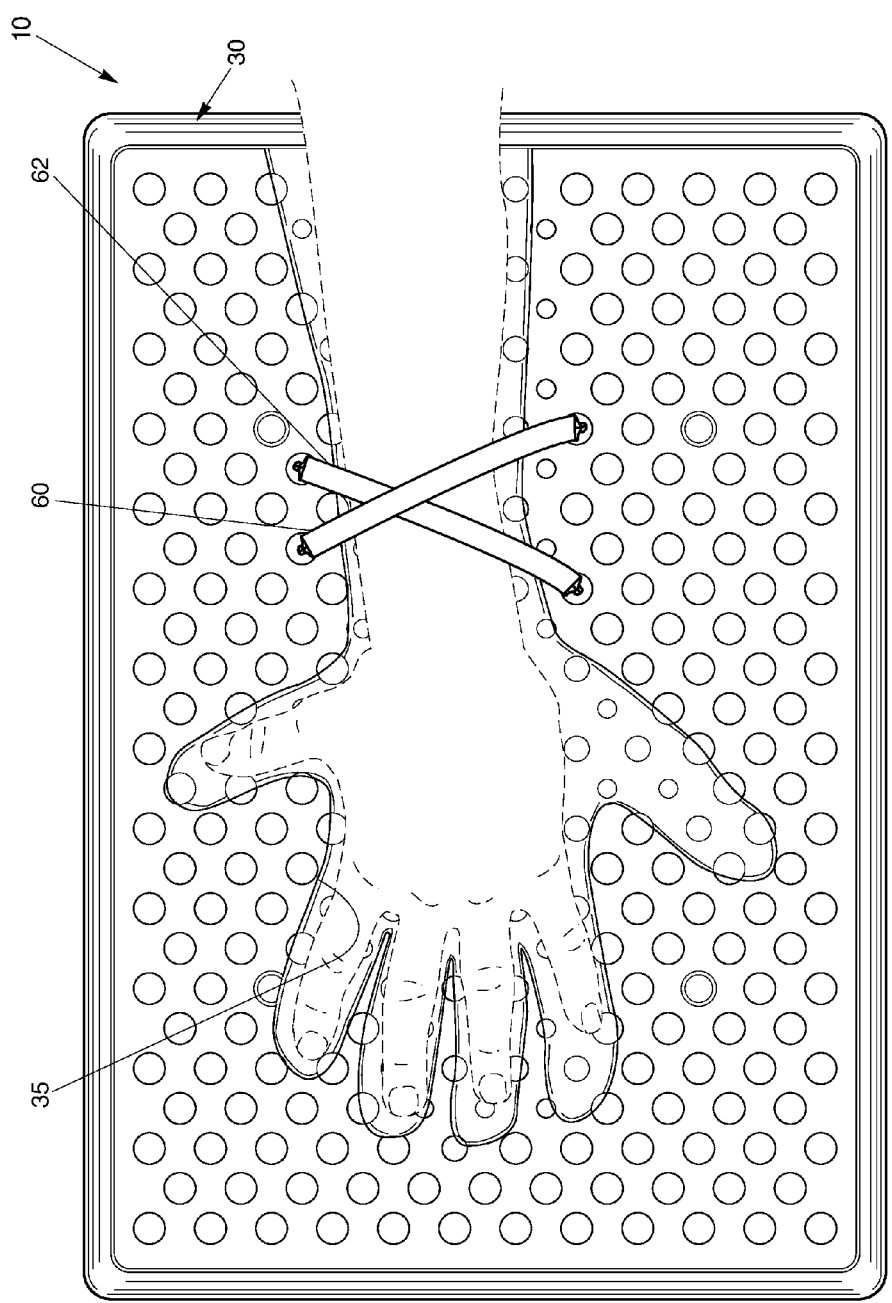
FIG. 11 is a top view of the debridement platform as shown in FIG. 10 with strap members securing the extremity.

Referring to FIG. 11, a flexible strap member 60, 62 for securing the extremity to the platform may engage at least one cover aperture 33. The strap member 60, 62 includes a means for fastening at a proximal and distal ends of the strap member 60, 62 within the at least one cover aperture 33. The means for fastening at a proximal and distal ends of the strap members 60, 62 may include fasteners or other devices known in the art. For example, a hook may be used to secure the proximal or distal end of the strap member 60, 62 within the at least one cover aperture 33.

Figure 12:
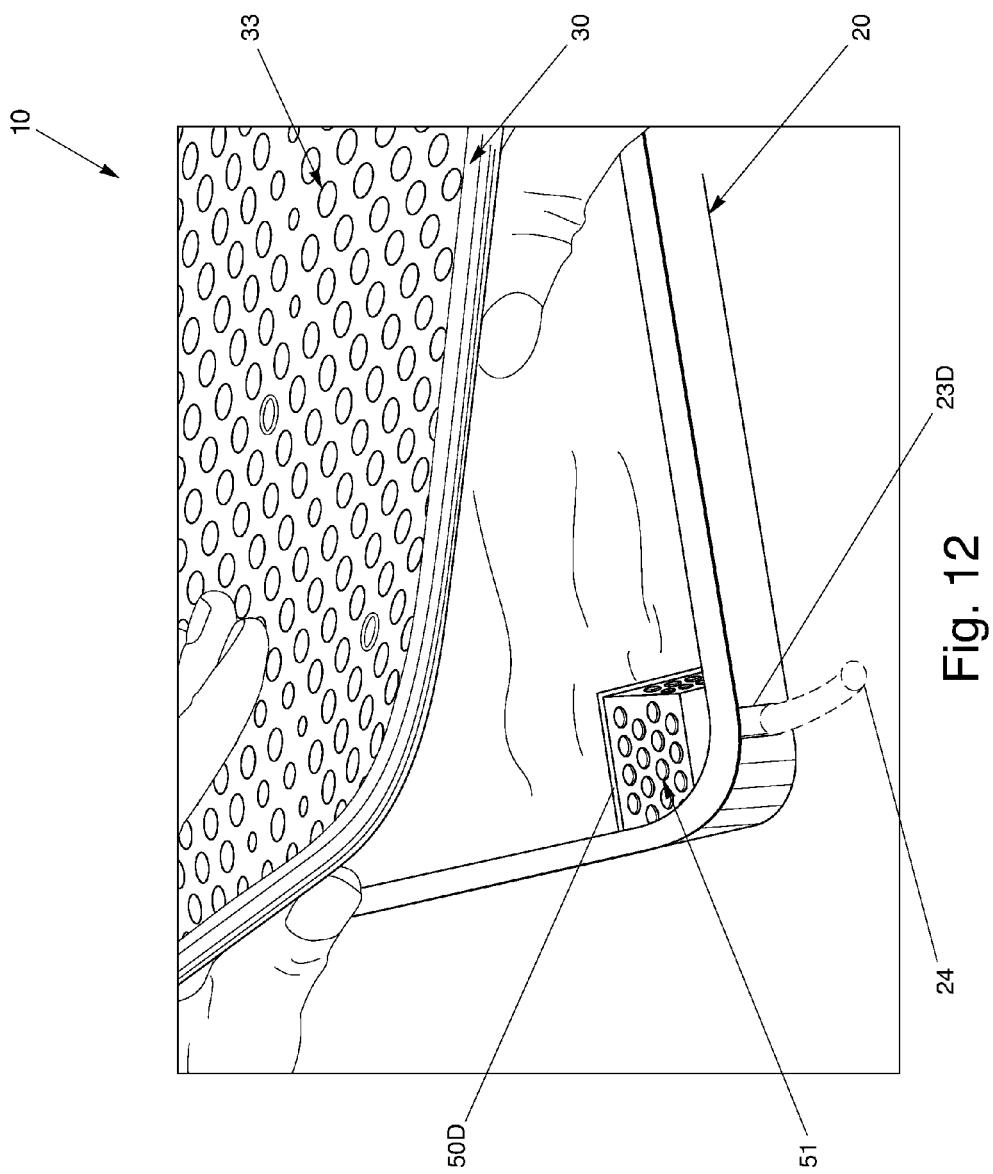
FIG. 12 is a perspective view of the debridement platform with the cover member being curled back for unclogging drainage tube.

Referring to FIG. 12, the cover member 30 is sufficiently pliable for curling a portion of the cover member 30 proximal to the at least one drainage aperture (23A, 23B, 23C, 23D) to provide access to the interior of the body member 20 for removing clogging debris from the filtration trap (50A, 50B, 50C, 50D) and drainage tube 24 while maintaining the extremity (not shown) on the cover member 30. By locating the filtration trap (50A, 50B, 50C, 50D), at least one U-shaped drainage aperture (23A, 23B, 23C, 23D), and drainage tube 24 in corner areas of the platform 10, a physician can more easily remove the drainage tube 24 for cleaning and remove debris from the filtration traps (50A, 50B, 50C, 50D).

Figure 13:
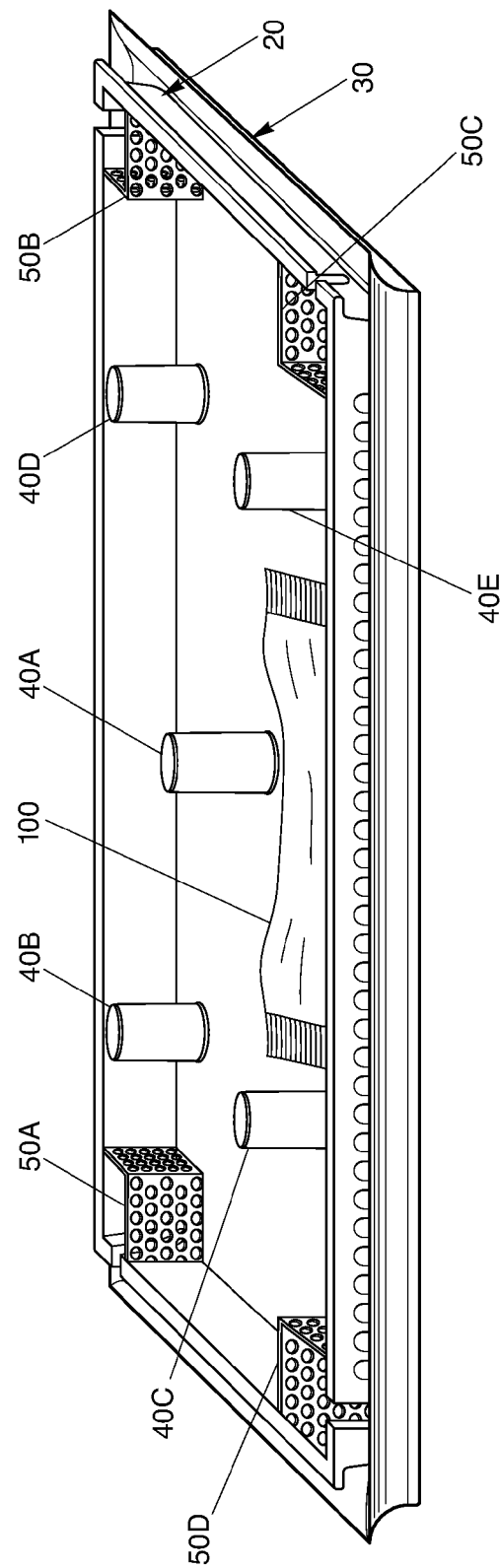
FIG. 13 is a perspective view of the debridement platform in a kit.

Referring to FIG. 13, a debridement surgical support kit for extremities of a human or mammal to assist a physician in treating an extremity may include the platform 10, as described herein, along with a surgery medical pack 100. The platform 10 including the body member 20 and the cover member 30. The cover member 30 nested with the body member 20 or the body member 20 nested within the cover member 30 to reduce the height of the platform 10 to a lower profile for more efficient transport. The surgery medical pack 100 including means for debridement and lavage of an extremity of a human known in the art such as surgical tools and other known surgical products for debridement and lavage. The surgery medical pack 100 is positioned within an interior of the nested platform to facilitate transport and reduce overall profile. A box having a low profile may be used for containing the nested platform and surgery medical pack 100 for purposes of transporting and storing the kit until required for surgery in a medical facility or storage area. In addition, one or more platforms 10 may be stackable within one another to further reduce consumption of valuable space within a medical facility, especially a surgical environment.

Figure 10:
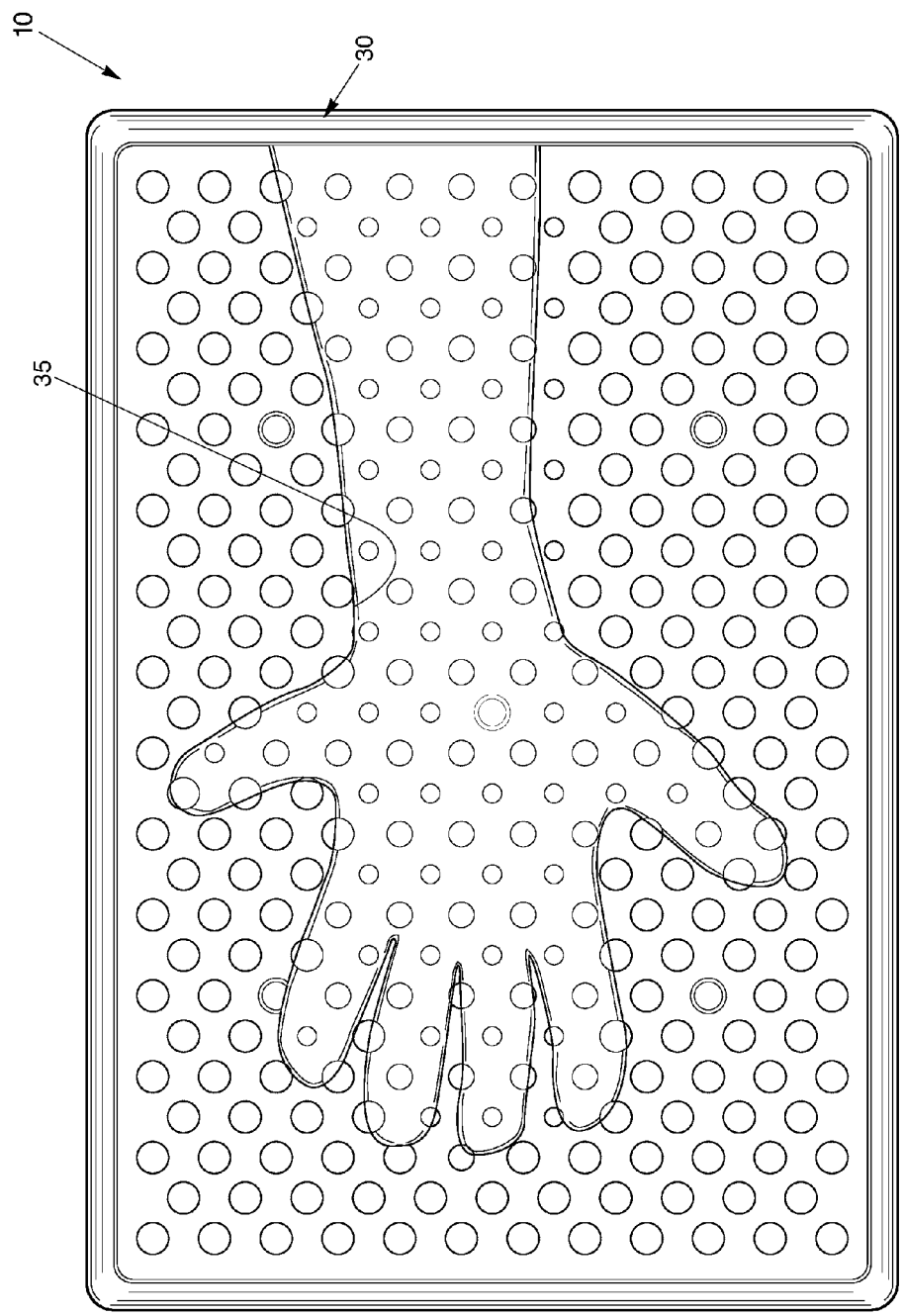
FIG. 10 is a top view of the debridement platform as shown in FIG. 1 with extremity recessed area defined therein.

In operation, the extremity is positioned upon an upper surface of the cover member 30 to facilitate the process of debridement and lavage of extremities. Referring to FIG. 10, the extremity is seated within the predefined recessed area 35 for additional support. The strap members 60, 62 are then secured over the top of the extremity within the at least one cover aperture 33. During cleaning and debridement, the fluid travels through the at least one cover aperture 33 for temporary storage within an interior of the body member 20. Next, the fluid passes through the filtration trap (50A, 50B, 50C, 50D) to capture any debris which could potentially clog the drainage tube. The fluid then exits the body member 20 through the drainage tube 24 positioned within the drainage aperture (23A, 23B, 23C, 23D) for proper disposal of the fluid, after it exits the drainage tube 24, by a variety of methods known in the art. If the drainage tube 24 becomes clogged, a user curls or slightly opens a corner portion of the cover member 30 to reveal a corner area of the body member 20 where the filtration trap (50A, 50B, 50C, 50D) can be cleaned in place or removed for cleaning, the draining aperture (23A, 23B, 23C, 23D) can be cleaned, and the drainage tube 24 can be removed. Most importantly, the extremity may continue to be positioned on the cover member 30, if desired, during the cleaning and unclogging of the drainage tube 24, filtration trap (50A, 50B, 50C, 50D), and drainage aperture (23A, 23B, 23C, 23D).

By way of example only and without limiting the present invention to these specific dimensions, one embodiment of the debridement platform 10 may have the following dimensions. These dimensions are merely an example and in no way limit the scope of this invention. A multitude of different heights, sizes, or diameters may be used in conjunction with the present invention. The dimensions of the body member 20 is 1.5 inches tall×14 inches wide×22 inches long and the dimension of the lid member is approximately 0.25-0.50 inches tall×14 inches wide by 22 inches long. The dimension of the splash flange or guard 34 is 0.030 to 0.060 inches. The at least one support member (40A, 40B, 40C, 40D, 40E) is 2 inches in diameter and 1.25 inches-1.325 inches tall. Note, the at least one support member (40A, 40B, 40C, 40D, 40E) positioned in a central portion of the body member 20 is 1.25 inches tall with the other at least one support member (40A, 40B, 40C, 40D, 40E)s 1.325 inches tall to allow for a slight concavity of the cover member 30. At least one cover aperture 33 defined within the cover member 30 having a range of 0.125 diameter to 0.750 diameter.

The body member 20 and the cover member 30 can be made from metal, plastic or other suitably flexible or semi-flexible and fluid impermeable material which may be disinfected or sterilized if desired. Exemplary materials which may be used in construction of both are polyethylene, polycarbonate and stainless steel. Manufacturing methods include but are not limited to injection molding and stamping. The platform 10 is made of material selected from a variety of materials including polycarbonate, HDPE (high density polyethylene), low density polyethylene, plastic materials, biodegradable materials, regrind materials, and recycled plastic materials in combination or alone. Also, the platform 10 is injection molded using plastic materials to accommodate a wide range of extremity sizes and types at a lower cost.

In another embodiment, referring now to FIGS. 14-18, the present invention provides surgical support debridement platform for extremities of a human to assist a physician in treating such extremity which incorporates the advantages and benefits of the above-mentioned platforms.

The platform includes a body member having a bottom end and at least one side wall. The body member defines an interior volume for temporarily containing fluid. In one embodiment, a depth of the body member maybe 2-3 cm to define a low profile. At least one drainage aperture is defined within the body member or second member for draining said fluid from the interior of said body member. The extremity is positioned upon a surface of the platform to facilitate the process of debridement and lavage of extremities.

Figure 14:
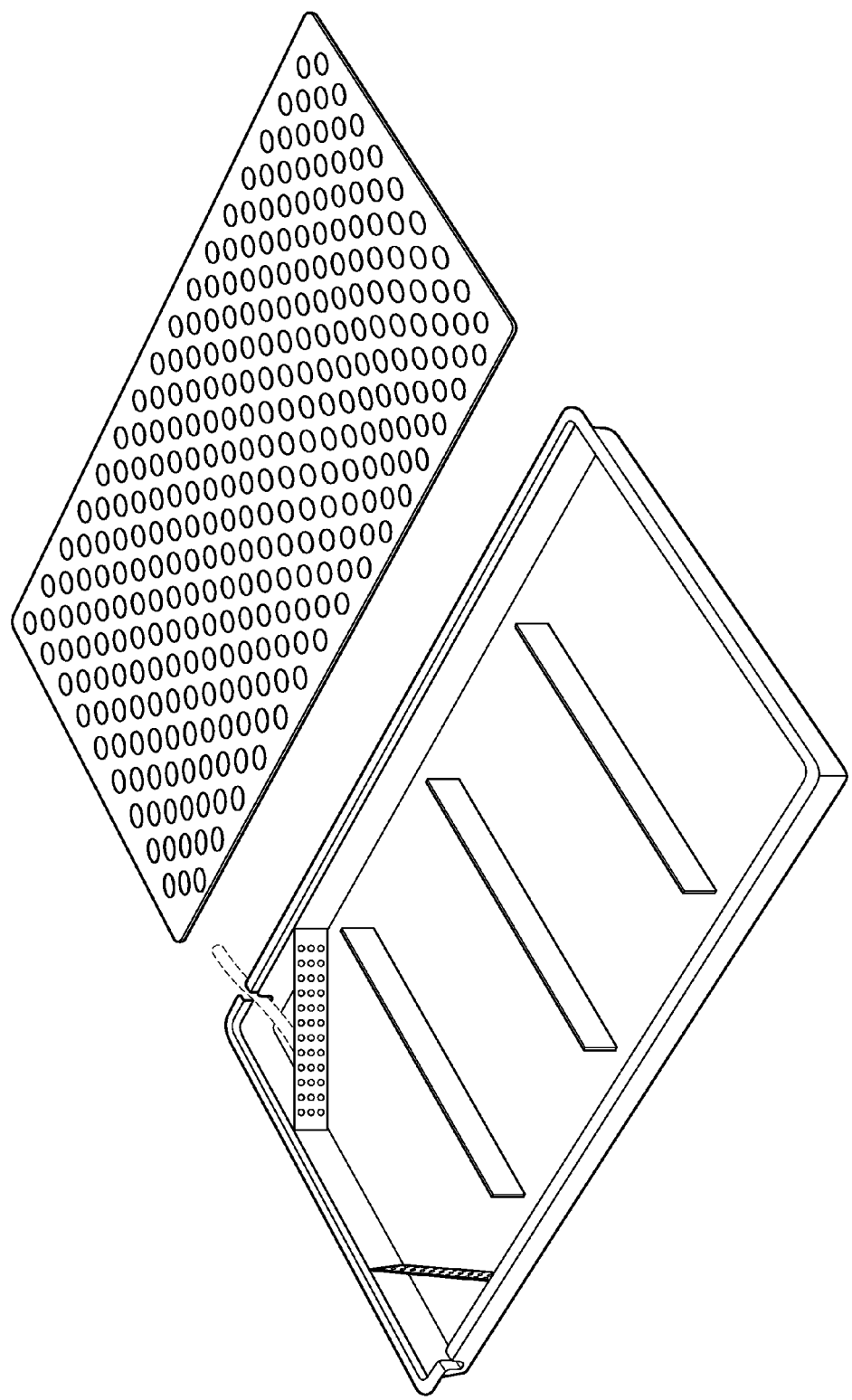
FIG. 14 is an exploded view of another embodiment of the debridement platform.

Referring to FIG. 14, the body member and cover member may include an alternative support member. In one embodiment, the support members are configured as wall members raised upon a surface of the body member. For example, the support wall members may be parallel to one another and have a raised profile sufficient to support a cover member. The support wall members may, in another embodiment, include one or more wall members having consistent lengths and heights to provide stability to the cover member. Alternatively, the support wall members may have varying lengths and heights to support the cover member. In addition, the cover member may nest or engage within an interior surface of the body member to provide a more secure fit. Also, the body member may define cut-outs or ports to receive a suction hose.

Figure 15:
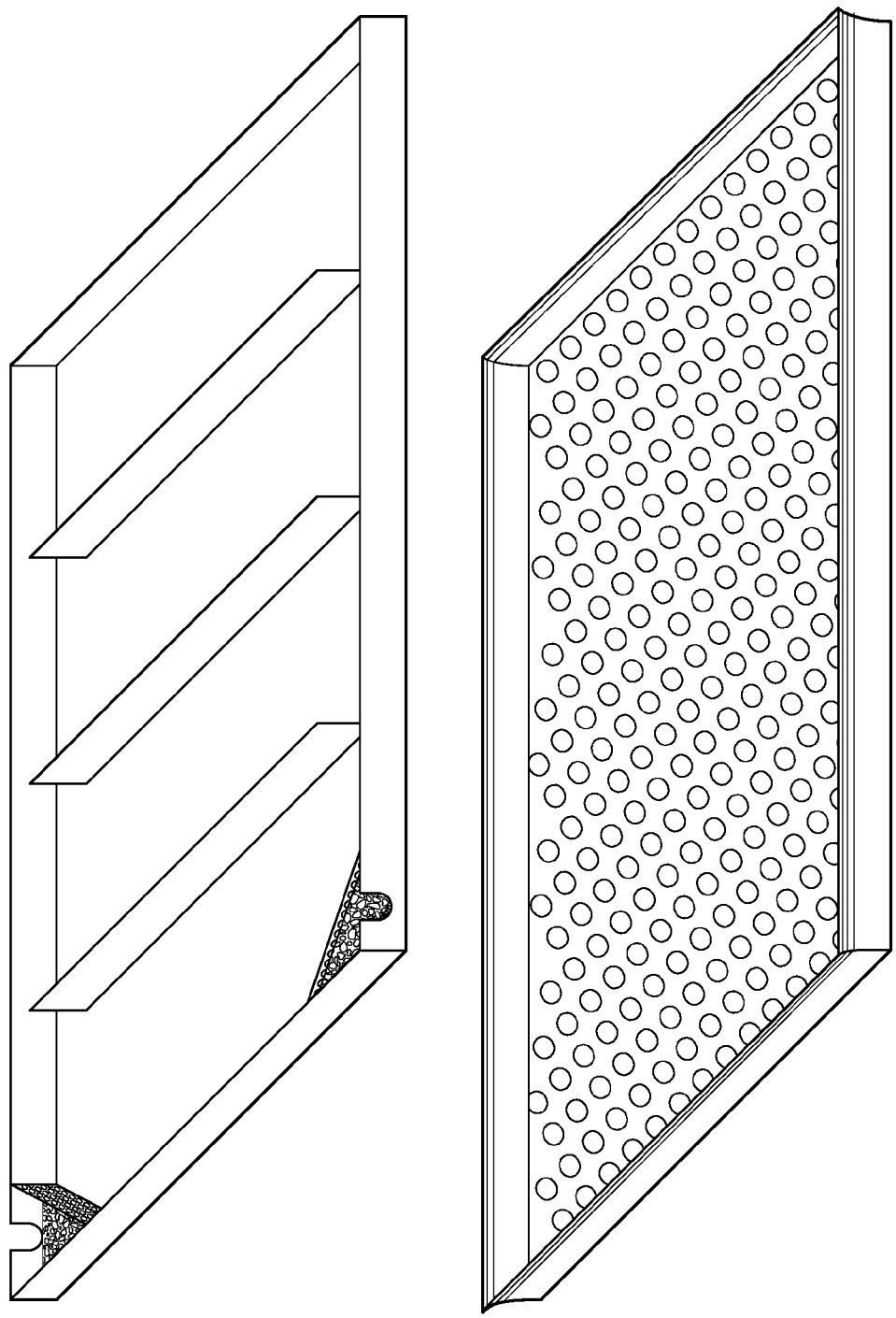
FIG. 15 is an exploded view of still another embodiment of the debridement platform.

Referring now to FIG. 15, the body member may define one or more suction tube portals and filter traps surrounding the suction tube portal area. Furthermore, an interior area between the filter traps and the section tube portal area may include a porous, or open cell material, such as foam to prevent clogging of the suction hose. For example, the porous material may be a variety of foam materials or composites of open cell or porous materials. It is also contemplated that the body member may include or not include filter traps and instead use open cell or porous materials to catch debris from entering into the suction tube and thereby clogging.

The open cell or porous materials may be dispersed or positioned about an interior surface of the body member in a variety of configurations depending upon the extremity and its size or other requirements. The open cell or porous material may also act as a cushioning surface to prevent direct contact with a surface of the body member, cover member, or both. Furthermore, it is contemplated that the open cell or porous material may be sandwiched between a cover member and the body member to secure the open sell or porous material within the platform. In another embodiment, the foam or open cell material may be dispersed with antimicrobial or antibacterial coatings. For example, the antimicrobial coating may be antimicrobial silver.

Alternatively, the open cell or porous material may be located on any surface of the cover member or body member. For example, the open cell material may be foam, more specifically polyurethane foam. Alternatively, materials other than open cell materials or porous materials may be used if the materials are configured to facilitate debridement and lavage of extremities. In one embodiment, foam or other suitable materials may be used within on a surface area of the body member, alone, or in combination with a second member. In another embodiment, foam or other suitable materials, may be used in combination with a basin or tray.

Figure 16:
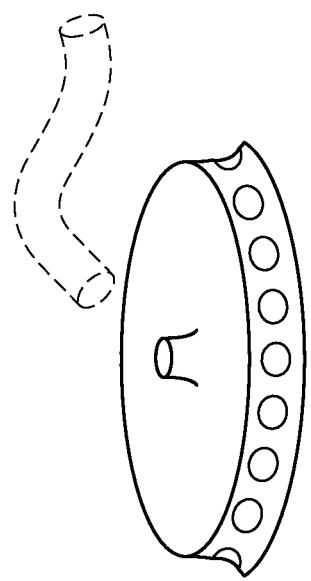
FIG. 16 is a perspective view of a suction pad used in conjunction with any debridement platform with the suction hose detached.

Referring now to FIG. 16, a suction pad may be connected proximal to a lower portion of the body member to facilitate removal of liquid. The suction pad may be held within an interior of the body member by adhesives, fasteners, weights, or other securing mechanisms or methods for retaining the suction pad within a lower portion of the body member. The suction pad may be made of solid or pliable materials, such as plastic. In one embodiment, the suction pad includes a nipple area or receiving area for suction tubing. The suction pad may also be engaged to or connected with a porous or open cell material. In one embodiment, the suction pad is situated on foam, porous, or other open cell material to provide distance between a bottom end of the body member and an interior of the suction pad.

Figure 17:
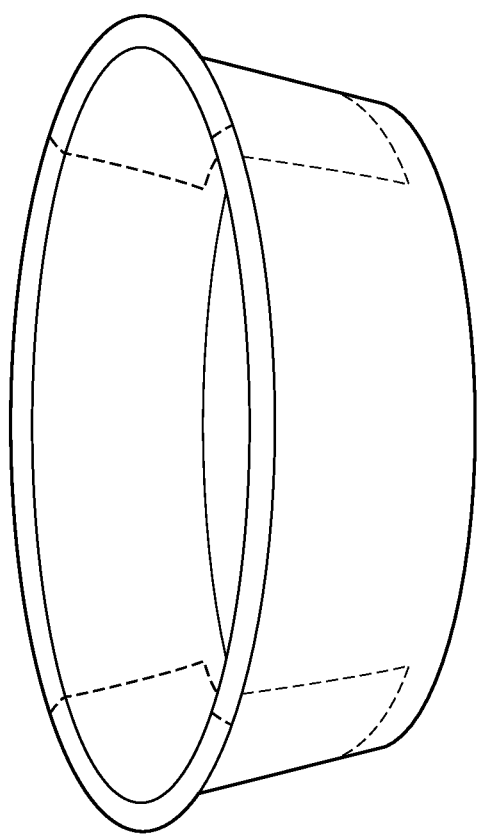
FIG. 17 is perspective view of another embodiment of the debridement platform with perforated sectional flap areas.

Referring now to FIG. 17, the body member, in one embodiment, may define a shape of a basin. Alternatively, the body member may be combined with a second member to provide a platform. The second member, in one embodiment, may be another basin, tray, cover member, or any of a number of other items used in conjunction with the body member to facilitate the debridement and lavage of an extremity.

Figure 18:
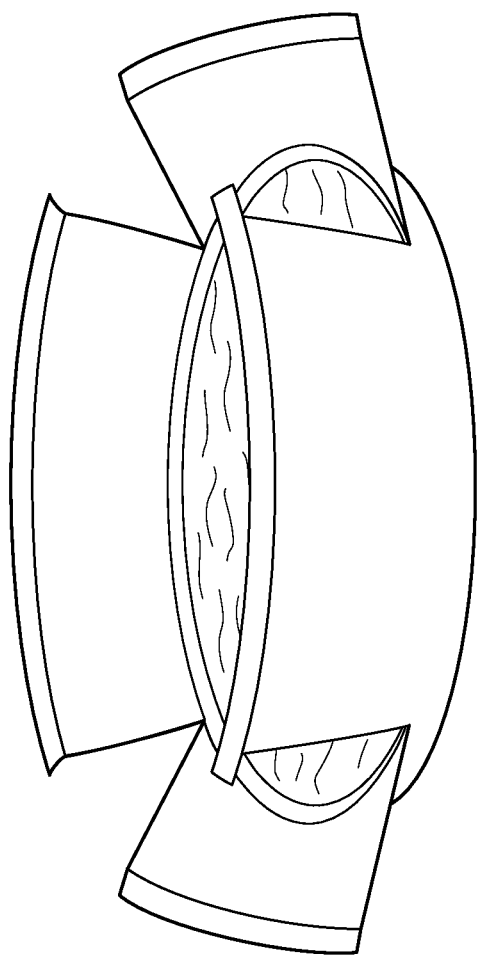
FIG. 18 is a perspective of FIG. 17 with the sectional flap areas turned outward.

Referring to FIGS. 17-18, a portion of the body member may define perforations or cut-outs to facilitate removal of one or more sectional flap areas of the body member. For example, two opposing portions of the body member may be removed or hinged away to provide a defined path to position an extremity within the body member. The sectional flap areas may be hinged outward to remove the side wall portion of the body member. Alternatively, the sectional flap areas may be removed or turned inward to guide an extremity within an interior of the body member. In another embodiment, the body member may be pre-formed with the side wall portions of the body member removed in advance of use.

Furthermore, an interior of the body member may include an open cell or porous material, such as polyurethane foam. The foam may be situated or dispersed about a surface of the body member. The body member may also include a second member, such as a cover member, basin, tray, or other items to be used in conjunction with the body member to facilitate the debridement and lavage of an extremity. The second member may cover, nest, or otherwise engage the body member.

It would be appreciated by those skilled in the art that various changes and modifications can be made to the illustrated embodiments without departing from the spirit of the present invention. All such modifications and changes are intended to be covered by the appended claims.

What is claimed is:

1. A portable surgical support debridement platform for supporting extremities of a human to assist a physician in treating such extremity, comprising:
   a body member including a bottom end and at least one sidewall,
   a cover member including an upper surface, the upper surface of the cover member configured to engage an extremity, said cover member releasably engaged to said body member, with the upper surface of said cover member defining an overall concave shape to prevent pooling of a fluid about an extremity;
   said body member and said cover member together defining an interior volume for temporarily containing the fluid;
   at least one drainage aperture for draining said fluid from the interior;
   the cover member and the body member together are portable and define an overall low profile for easier engagement under an extremity and visibility of the extremity;
   at least one cover aperture defined within said cover member for facilitating a flow of the fluid through the cover member and into the interior;
   whereby the extremity is positioned upon the upper surface of said cover member to facilitate the process of debridement and lavage of extremities while, at the same time, supporting the extremity.

2. The platform of claim 1, wherein said at least one drainage aperture generally defines a U shape.

3. The platform of claim 2, wherein said at least one drainage aperture is positioned proximal to a corner area of said body member, said drainage aperture positioned in a lower portion of said sidewall substantially proximal to said bottom end of said body member.

4. The platform of claim 3, wherein said cover member is sufficiently pliable for curling upward proximal to said at least one drainage aperture to provide access to the interior for removing clogging debris and drainage tube while maintaining the extremity on said cover member.

5. The platform of claim 1, further comprising a suction pad proximal to a lower portion of the body member to facilitate removal of a fluid.

6. The platform of claim 5, wherein the suction pad includes a nipple area for receiving suction tubing.

7. The platform of claim 1, wherein the cover member releasably engages the body member by nesting within a surface of the body member.

8. The platform of claim 1, wherein the at least one cover aperture has a smaller diameter within an extremity area.

9. The platform of claim 1, further comprising:
   a flexible strap member for securing said extremity to said platform.

10. The platform of claim 1, further comprising:
    an open cell material proximal to said at least one drainage aperture in said platform to prevent clogging of a drainage tube positioned within said at least one drainage aperture for draining said fluid from the interior.

11. The platform of claim 1, wherein said cover member predefines a recessed extremity area for providing further stability to an extremity while seating on said cover member.

12. The platform of claim 1, wherein said platform is made of material selected from a group consisting of: polycarbonate, HDPE (high density polyethylene), low density polyethylene, plastic materials, biodegradable materials, regrind materials, and recycled plastic materials in combination or alone.

13. The platform of claim 1, wherein said cover member has a low-profile splash guard positioned along an outer periphery of said cover member.

14. The platform of claim 1, wherein said cover member and said body member are configured of flexible materials to cushion the extremity for comfort.

15. The platform of claim 1, wherein a filtration trap includes at least one wall surrounding a perimeter of the at least one drainage aperture positioned on or above the body member.

16. The platform of claim 1, wherein the body member defines a shape of a basin.

17. The platform of claim 1, wherein the body member provides a defined path to position an extremity.

18. The platform of claim 1, wherein the body member includes an open cell material.

19. The platform of claim 1, wherein the body member includes a porous material.

* * * * *